US012635970B2

(12) United States Patent
Mashood et al.

(10) Patent No.: US 12,635,970 B2
(45) Date of Patent: May 26, 2026

(54) SYSTEM FOR NON-INVASIVE CALIBRATION-FREE BLOOD PRESSURE (BP) MEASUREMENT

(71) Applicants: Healthcare Technology Innovation Centre, Taramani (IN); Indian Institute of Technology Madras (IIT Madras), Chennai (IN)

(72) Inventors: Nabeel Pilaparambil Mashood, Taramani (IN); Jayaraj Joseph, Chennai (IN); Rahul Manoj, Taramani (IN); Raj Kiran Vangapandu, Taramani (IN); Mohanasankar Sivaprakasam, Chennai (IN)

(73) Assignees: Healthcare Technology Innovation Centre, Taramani (IN); Indian Institute of Technology Madras (IIT Madras), Chennai (IN)

( * ) Notice: Subject to any disclaimer, the term of this patent is extended or adjusted under 35 U.S.C. 154(b) by 66 days.

(21) Appl. No.: 18/019,158

(22) PCT Filed: Jul. 26, 2021

(86) PCT No.: PCT/IN2021/050727
§ 371 (c)(1),
(2) Date: Feb. 1, 2023

(87) PCT Pub. No.: WO2022/029793
PCT Pub. Date: Feb. 10, 2022

(65) Prior Publication Data
US 2023/0329667 A1 Oct. 19, 2023

(30) Foreign Application Priority Data
Aug. 5, 2020 (IN) .............................. 202041033513

(51) Int. Cl.
*A61B 8/04* (2006.01)

(52) U.S. Cl.
CPC ..................................... *A61B 8/04* (2013.01)

(58) Field of Classification Search
CPC ....................................................... A61B 8/04
See application file for complete search history.

(56) References Cited

U.S. PATENT DOCUMENTS

| | | | | |
|---|---|---|---|---|
| 6,176,832 B1 * | 1/2001 | Habu | ................... | A61B 5/0285 |
| | | | | 600/490 |
| 6,875,176 B2 * | 4/2005 | Mourad | ............... | A61B 5/4064 |
| | | | | 600/442 |

(Continued)

FOREIGN PATENT DOCUMENTS

| | | | | |
|---|---|---|---|---|
| WO | WO-2014030174 A2 * | 2/2014 | ......... | A61B 5/02007 |
| WO | WO-2015193917 A2 * | 12/2015 | ........... | A61B 8/5223 |

OTHER PUBLICATIONS

Mukkamala, R., et al. "Towards Ubiquitous Blood Pressure Monitoring via Pulse Transit Time: Theory and Practice," IEEE Trans Biomed Eng. vol 62(8), 2015. p. 1879-1901 (Year: 2015).*

*Primary Examiner* — Sean A Frith
(74) *Attorney, Agent, or Firm* — Nath, Goldberg & Meyer; Joshua B. Goldberg

(57) ABSTRACT

A system for measurement of non-invasive and calibration-free blood pressure (BP) is disclosed. The system comprises a measurement probe (302) which is in contact with a person's skin. The measurement probe (302) comprises a first array of sensors (302-1) and a second array of sensors (302-2). The first array of sensors (302-1) determines a force exerted on skin (304) and the second array of sensors (302-2) determines a compression-decompression characteristics of the arteries through skin. The force exerted on skin and the compression-decompression characteristics of the arteries are used to determine indices indicative of the material properties of the vessel. Based on the indices indicative of the material properties of the vessel, blood (Continued)

pressure and continuous transmural pressure waveform may be determined.

14 Claims, 4 Drawing Sheets

(56)                    References Cited

U.S. PATENT DOCUMENTS

2012/0108983  A1      5/2012   Banet et al.
2017/0156706  A1*     6/2017   Joseph  ............... A61B 5/02125
2019/0076113  A1*     3/2019   Palanisamy  ............ A61B 8/488

* cited by examiner

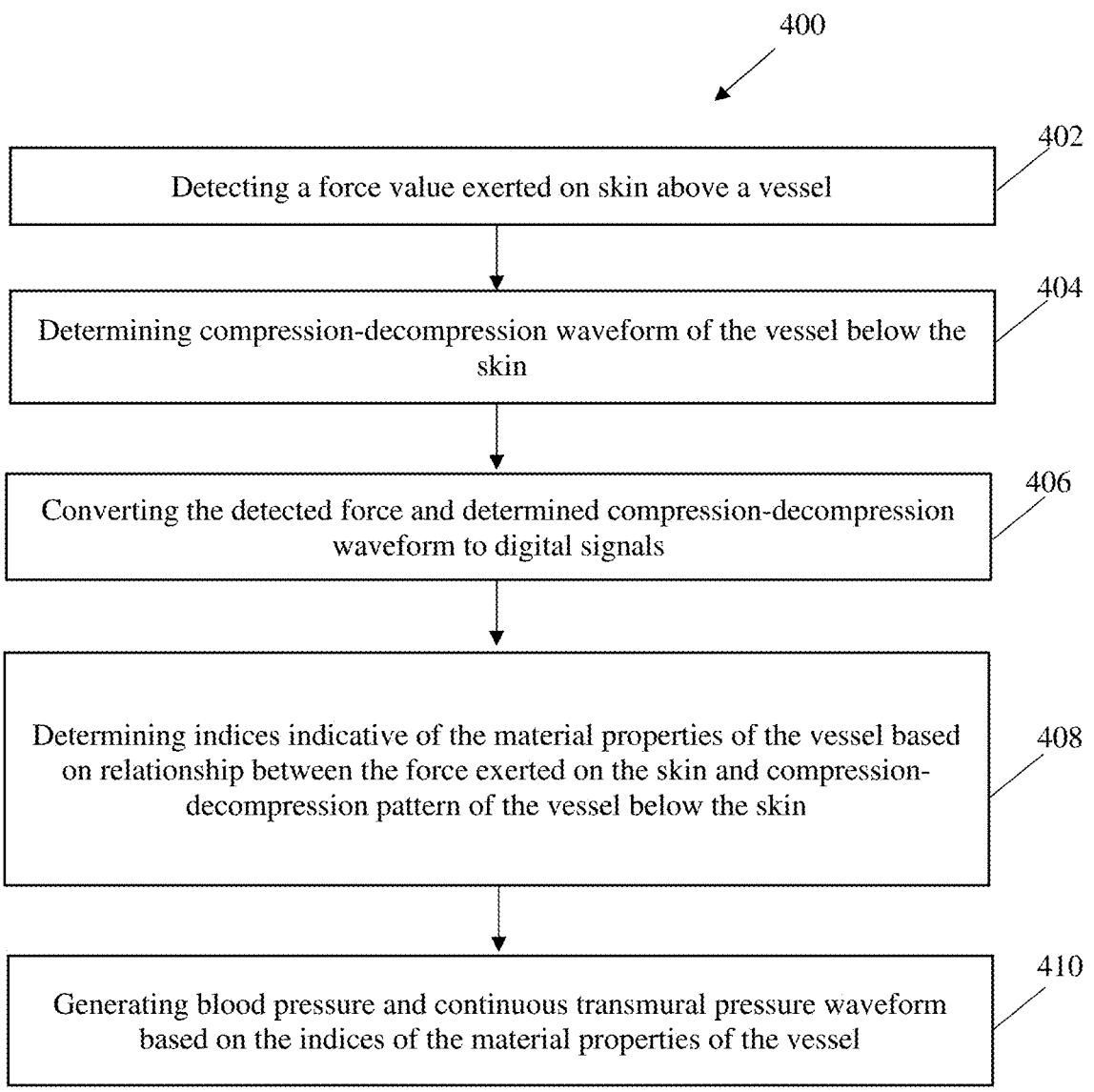

400

402

Detecting a force value exerted on skin above a vessel

404

Determining compression-decompression waveform of the vessel below the skin

406

Converting the detected force and determined compression-decompression waveform to digital signals

408

Determining indices indicative of the material properties of the vessel based on relationship between the force exerted on the skin and compression-decompression pattern of the vessel below the skin

410

Generating blood pressure and continuous transmural pressure waveform based on the indices of the material properties of the vessel

Figure 4

SYSTEM FOR NON-INVASIVE CALIBRATION-FREE BLOOD PRESSURE (BP) MEASUREMENT

FIELD OF INVENTION

Embodiments of the present application illustrate a system and method for non-invasive and calibration-free measurement of blood pressure.

BACKGROUND OF THE INVENTION

Blood pressure is used in various diagnostics and treatment method employed by medical practitioners. The blood pressure (BP) is generally measured by a pressure cuff applied at a brachial artery of a person. However, studies of cardiovascular physiology have shown that an absolute BP level varies throughout an arterial system of a person due to the pulse pressure amplification effect. The pulse pressure amplification effect phenomenon is a combined effect of progressive changes in elastic behaviour and geometry of the arterial vessels from the central to the peripheral sites, and multiple reflections of transit pressure waves over long arterial segments composed of multiple vessels with different mechanical characteristics. Consequently, BP parameters assessed from the brachial artery using conventional devices, such as pressure cuffs, are a poor indicator for central aortic pressure or central BP, which is the pressure directly exerted on vital organs.

The central BP is measured by arterial catheterisation, popularly known as A-line or arterial line. Arterial catheterisation is further classified into extravascular and intravascular methods based on the location of a sensing element. In both the methods, a physician inserts a catheter by means of a surgical cut or percutaneous insertion. In the extravascular method, the sensing element remains outside of the artery, connected to a liquid-filled catheter via a tube. The sensing element measures the pressure exerted, by blood, on the catheter liquid. The sensing element is required to be periodically flushed by a saline-heparin solution to avoid any clotting of blood at the sensing surface of the sensing element. Thus, in this case, the accuracy of measurement of the BP is limited by the hydraulic properties of the catheter liquid. Further, there is an additional time delay in recording of BP due to response characteristics of the catheter liquid. In the intravascular method, the sensing element is located at the tip of the catheter and inserted into the artery. The intravascular method does not depend upon any intermediate catheter liquid. Thus, the measured BP is more accurate and has less time delay. However, the downside of the intravascular method is higher cost and limited reusability. Arterial catheterisation is an invasive technique and is limited for critically ill persons and are mainly used in surgical procedures. The risk associated with this invasive procedure includes pain, swelling, accidental dislodgement, thrombosis, catheter-related infection etc.

SUMMARY OF THE INVENTION

The following presents a simplified summary of the subject matter in order to provide a basic understanding of some of the aspects of subject matter embodiments. This summary is not an extensive overview of the subject matter. It is not intended to identify key/critical elements of the embodiments or to delineate the scope of the subject matter. Its sole purpose is to present some concepts of the subject matter in a simplified form as a prelude to the more detailed description that is presented later.

The present invention discloses a system and method for non-invasive calibration-free measurement of blood pressure (BP).

According to the present subject matter, the system comprises a measurement probe which is in contact with a body part of a person. In an example, the measurement probe may be non-invasively attached to or placed on the skin of a person over the blood vessel. The measurement probe comprises a first array of sensors to measure a force exerted by a vessel on the skin of the person and a second array of sensors to measure the compression and decompression pattern of the vessel below the skin. The first and second array of sensors may have at least one sensor. Further, non-linear relationships are developed based on the force exerted on the skin and the compression-decompression pattern of the vessel below the skin. Based on the non-linear models, indices indicative of the material properties of the vessel are determined. Finally, blood pressure and continuous transmural pressure waveform is generated based on the indices of the material properties of the vessel.

Thus, the present subject matter takes into account the wall dynamics, inertial characteristics and the geometrical waveforms of the vessel to measure blood pressure, which when applied to arteries close to heart or nearby branches yields more accurate estimate of continuous blood pressure. Further, the system of the present subject matter is a non-invasive technique and the blood pressure is directly measured from the surface of the skin above the vessel. Also, a calibration of blood pressure is not required, as it is directly calculated based on the hemodynamic curves constructed from the measured parameters and a set of biomechanical models that relate these curves to the transmural pressure.

BRIEF DESCRIPTION OF THE ACCOMPANYING DRAWINGS

The following drawings are illustrative of particular examples of the present disclosure and are not intended to limit the scope of the invention. The drawings are not to scale (unless so stated) and are intended for use in conjunction with the explanations in the following detailed description.

FIG. 4 illustrates a method for generating blood pressure and continuous transmural pressure.

Figure 1:
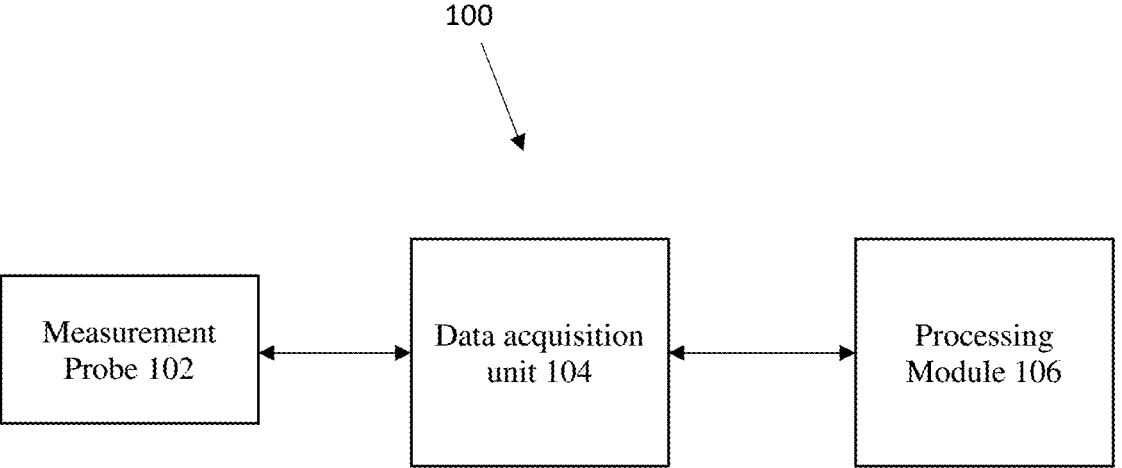
FIG. 1 shows a system 100 for measurement of a blood pressure and continuous transmural pressure waveform in an example implementation of the present subject matter.

Persons skilled in the art will appreciate that elements in the figures are illustrated for simplicity and clarity and may represent both hardware and software components of the system. Further, the dimensions of some of the elements in the figure may be exaggerated relative to other elements to help to improve understanding of various exemplary embodiments of the present disclosure. Throughout the drawings, it should be noted that like reference numbers are used to depict the same or similar elements, features, and structures.

DETAILED DESCRIPTION

Exemplary embodiments now will be described. The disclosure may, however, be embodied in many different forms and should not be construed as limited to the embodiments set forth herein; rather, these embodiments are provided so that this disclosure will be thorough and complete, and will fully convey its scope to those skilled in the art. The terminology used in the detailed description of the particular exemplary embodiments illustrated in the accompanying drawings is not intended to be limiting. In the drawings, like numbers refer to like elements.

FIG. 1 shows a system 100 for measurement of the BP. The system comprises a measurement probe 102. The measurement probe 102 may be hand-held or holder or strap or a patch that can be held in place or removably attached to a body part of a person. In an example, the measurement probe 102 may have an ergonomic design such that the measurement probe 102 may be conveniently attached to any body part of any person manually or by means of automated positioners. In an example, the measurement probe 102 may have an elastic body such that the measurement probe 102 may be easily attached to the person's body. In an example, the measurement probe 102 may have a fixing means to attach the measurement probe to the person's body. In another example, the measurement probe 102 may be hand-held to a person's body during the measurement procedure. In another example, the measurement probe 102 may be positioned using an automated positioners or robotic arm to a person's body during the measurement procedure.

The measurement probe 102 comprises a first array of sensors and a second array of sensors. The first array of sensors measures a force exerted by a vessel on skin. A second array of sensors captures compression-decompression pattern of the vessel. In an example the first array of sensors and the second array of sensors may have one or more sensors. In an example, the first array of sensors may be resistive or capacitive strain gauges, piezoelectric elements, optical vibrometers, or any combinations of such sensors. The second array of sensors may be ultrasonic sensors.

A data acquisition unit 104 captures the measurement provided by the first array sensors and the second array of sensors. The data acquisition unit 104 provides the captured measurement to a processing module 106.

The processing module 106 determines indices indicative of the material properties of the vessel based on the relationship between the force exerted on the skin and compression-decompression pattern of the vessel below the skin. The processing module 106 thereafter, generates blood pressure and continuous transmural pressure waveform based on the determined indices of the material properties of the vessel. The method is described below in detail.

To determine the blood pressure and continuous transmural pressure waveform, the processing module 106 determines instantaneous transit time and a pulse wave velocity of blood pulse wave within the vessel. Further, based on the instantaneous transit time and the pulse the wave velocity of blood pulse wave within the vessel at least one of a pressure value for a particular time instant in the pulse cycle, and a minimum pressure value, and a diastolic pressure value can be calculated. The processing module 106 also captures non-linear changes in the force detected on the skin and the compression-decompression pattern of the vessel below the skin to determine the indices of the material properties of the vessel. The non-linear changes are captured using any one of following relationships:

a. relation between the indices of the material properties of the vessel to the elastic component of instantaneous force detected on the skin, the peak change in the elastic component of the force and vessel diameter waveform, extrema of the diameter waveform or that relates b. relation between the indices of the material properties of the vessel to blood pulse wave velocity, vessel diameter, and relative change of force detected on the skin to diameter, respectively, at multiple time instants and the peak gradient of vessel diameter;

c. relation between the indices of the material properties of the vessel to the relative change in force detected on the skin to the vessel diameter and the vessel diameter gradient at multiple time instants Finally, based on the at least one of a pressure value for a particular time instant in the pulse cycle, a minimum pressure value, and a diastolic pressure value for each pulse cycle and the indices of the material properties of the vessel, the processing module 106 determines the blood pressure and continuous transmural pressure waveform. In an example, the data acquisition unit 104 may communicate with the measurement probe 102 via a wireless communication, such as an internet network, Bluetooth network, infrared network or any other near field communication techniques. In another example, the data acquisition unit 104 may be hardwired to the measurement probe 102.

Similarly, in an example, the data acquisition unit 104 may communicate with the processing module 106 via a wireless communication, such as an internet network, Bluetooth network, infrared network or any other near field communication techniques. In another example, the data acquisition unit 104 may be hardwired to the processing module 106.

Example embodiments for determining blood pressure and continuous transmural pressure waveform would be now described in detail. An example implementation for calculating blood pressure and continuous transmural blood pressure is described below.

In an example, to determine blood pressure and continuous transmural pressure, the processing module 106 constructs hemodynamic curves models using the detected force on the skin surface and the compression-decompression pattern of the artery. In an example, a relationship between elastic component of the blood pressure acting on arterial wall can be represented by $P_e(t)$ and its skin surface force component can be represented by $f_e(t)$ (force on skin). A relationship between $P_e(t)$ and $f_e(t)$ can be expressed as:

$$P_e(t) = A_1 \times f_e(t) + B_1$$

wherein $A_1$ and $B_1$ are constants.

The processing module 106 may determine hemodynamic curves at multiple sites of a target artery and may determine the value of the constants $A_1$, $B_1$ and $f_e(t)$ using models derived from hemodynamic curves. Hence, all the independent terms in the above equation (A, B, and $f_e(t)$) are directly obtained by using the signals detected by the measurement probe. Therefore, the blood pressure component $P_e(t)$ can be calculated by direct measurement of all desired signals from the arterial site. The methods for calculating the blood pressure has been described in detail with reference to FIGS. 2a and 2b.

Figure 2:
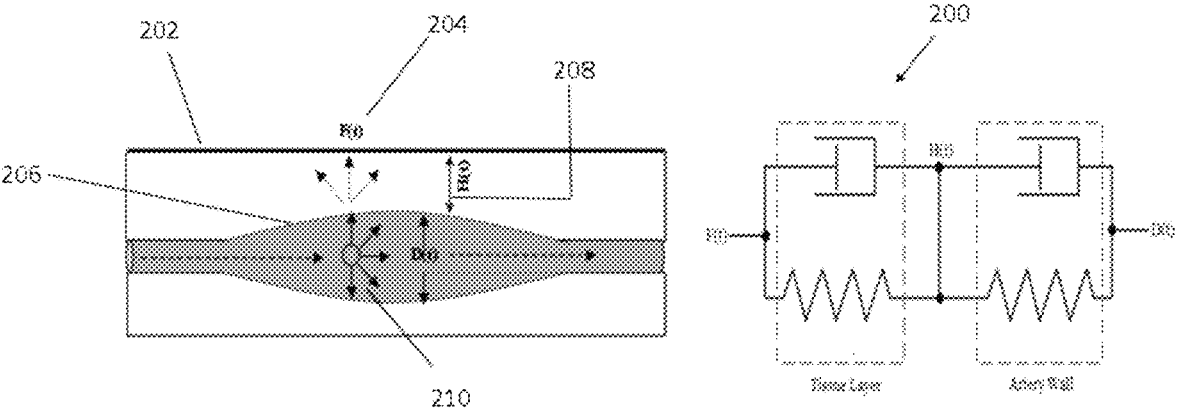
FIG. 2a shows an area of body of a person for which measurement of a blood pressure continuous transmural pressure waveform is done in an example implementation of the present subject matter.
FIG. 2b shows a model 200 for measurement of the blood pressure and the continuous transmural pressure waveform in an example implementation of the present subject matter.

According to the present subject matter, a spring-damper arrangement of superficial blood vessel (such as, carotid artery, brachial artery, radial artery, femoral artery, etc.) and its surrounding biomaterials can be modelled as shown in FIG. 2b. FIG. 2a shows a corresponding area of person's body based on which the spring-damper model is modelled. For simplicity a single model is shown in the FIG. 2b and it should be understood that a plurality of such models would represent a region on a person's body. A constant force that acts on a skin surface 202 can be represented by f(t) 204. When a constant external force f(t) 202 acts on the skin surface 202, a thickness of region between a skin surface and a proximal wall 206 of an artery or a vessel is represented by H(t) 208. The thickness of region between a skin surface 202 and a proximal wall of the artery compresses and decompresses based on an expansion and contraction of the artery. The compression and decompression H(t) 208 varies in accordance with a quasiperiodic expansion/contraction of the artery's luminal diameter D(t) 210 subject to a pulsatile transmural pressure P(t) acting towards a radial direction. Therefore, compression-decompression pattern of H(t) may be expressed as; $H(t) \propto (1/D(t)) \propto 1/(P(t))$.

The transcutaneous force f(t) 204 acting on the surface and its elastic $f_e(t)$ and viscoelastic $f_v(t)$ components can be further modelled, as shown Equation (1), in terms of equivalent elastic modulus $E_S$ and viscoelastic coefficient $\eta_s$ for the layers between proximal wall of the arterial vessel and skin.

$$f(t) = f_e(t) + f_v(t) = E_s \times \frac{1}{H(t)} + \eta_s \frac{d}{dt}\left(\frac{1}{H(t)}\right) \quad (1)$$

A transcutaneous force f(t) 204 acting on the skin surface is an attenuated version of the transmural arterial pressure P(t). The degree of attenuation can be modelled as a polynomial function of P(t) with linear and non-linear arbitrary coefficients ($k_i$) reflecting the material properties of surrounding tissue like medium. The force f(t) 204 may be represented by following equation number 2:

$$f(t) = F\{P(t), k_1, \ldots, k_N\} \quad (2)$$

Based on the above equation, the elastic component of arterial pressure $P_e(t)$, the elastic component of transcutaneous force $f_e(t)$ may be expressed by following equation number 3:

$$f_e(t) = \frac{1}{A} P_e(t) - B \quad (3)$$

where A and B are constants which reflects attenuation and static offset levels. $f_e(t)$ is obtained measuring f(t) 204 using high-fidelity surface force sensors, and then eradicating any viscous component using model given in Equation (1) with the help of hemodynamic loop relating f(t) 204 and arterial diameter D(t) 210 or H(t) 208. Both D(t) 210 and H(t) 208 can be measured in synchronisation with f(t) 204 using various techniques. One of the techniques may be using ultrasound to measure D(t) 210 and H(t) 208. Further, constants in equation 3 should be eliminated to obtain the blood pressure $P_e(t)$.

According to the present subject matter, the above equation 3 can be safely rewritten in terms of a maximum amplitude change experienced by the transmural pressure and transcutaneous force as the observed attenuation affect their amplitude alone. The maximum changes in $P_e(t)$ and that in $f_e(t)$, denoted as $\Delta P$ and $\Delta f$, which can be further related to the diastolic blood pressure ($P_d$) as shown in Equation (4):

$$P_e(t) = \frac{\Delta P}{\Delta f} \times f_e(t) + P_d \quad (4)$$

Incorporating the non-linear relation of $P_e(t)$, D(t) 210, and specific stiffness index $\beta$ of the artery wall into the above model, a compressive expression relating $f_e(t)$ with $\beta$ can be developed as shown in Equation (5).

$$f_e(t) = \Delta f \left( \frac{e^{\beta\left(\frac{D(t)}{D_d} - 1\right)} - 1}{e^{\beta\left(\frac{D_s}{D_d} - 1\right)} - 1} \right) \quad (5)$$

In the above equation, all parameters, except $\beta$, can be measured using suitable sensor arrangements, such as a force-ultrasound system, with the help of a $f_e(t)$-D(t) hemodynamic loop. Thus, by optimizing the solution for Equation (5), the specific stiffness index $\beta$ of the artery wall is calculated. Thereafter, by performing an additional measurement of pulse wave velocity at the diastolic blood pressure level ($C_d$), the diastolic blood pressure is calculated using a formula $P_d = 2 \rho C_d^2/\beta$. Finally, according to the present subject matter, continuous transmural pressure waveform $P_e(t)$ may be calculated with the help of given $\beta$ and $P_d$ values using nonlinear pressure-diameter relationship of the form $P_e(t) = P_d$ exp ($\beta$*Gradient of lumen diameter). The procedure is applicable to each cardiac cycle, and hence the method of the present subject matter yields beat-by-beat values and continuous waveform of transmural blood pressure from the superficial arteries.

In accordance with another example implementation of the present subject matter, instantaneous pulse wave velocity can be represented by C(t). For a given cardiac cycle an example method to evaluate C(t) is by measuring the transit features including instantaneous transit time and blood pulse transit distance along the vessel. By incorporating the non-linear relationship between C(t), D(t) 210, and pressure gradient of the arterial wall 206 into Equation (4), and considering the relationship between $P_e(t)$, D(t) 210, and specific stiffness index $\beta$, a the relationship between $f_e(t)$, $\beta$, $P_d$ can be represented by Equation (6).

$$\frac{C_\psi^2}{D_\psi} \times 2\rho \times \frac{dD}{df}|_\psi = \frac{P_d}{f_{mx}} \times \left(e^{\beta\left(\frac{D_s}{D_d} - 1\right)} - 1\right) \quad (6)$$

where $\psi$ is a given arbitrary time instant within the cardiac cycle.

In this equation 6, all the parameters, except $\beta$ and $P_d$, can be measured using suitable sensor arrangements such as a force-ultrasound system using the help of a $f_e(t)$-D(t) 210 hemodynamic loop. Further, an additional measurement of pulse wave velocity at the diastolic blood pressure level ($C_d$) and at any other fiducial point ($C\psi$) is done. Subsequently, by numerically solving for of the system of equations comprising Equation (6) and the diastolic blood pressure equation $P_d = 2 \rho C_d^2/\beta$, specific stiffness index $\beta$ of the artery wall and diastolic BP ($P_d$) can be calculated. The continuous transmural pressure waveform $P_e(t)$ can be determined by using the fundamental pressure-diameter model with the help of $\beta$ and $P_d$ values. The above described procedure is applicable to each cardiac cycle, and hence the method yields beat-by-beat values of transmural blood pressure from the superficial arteries.

According to yet another example implementation of the present subject matter, incorporating the non-linear relation of $P_e(t)$, $D(t)$ 210, and specific stiffness index $\beta$ into Equation (4) and combining it with the non-linear relationship between $C(t)$, $D(t)$ 210 and pressure gradient of the arterial wall, a relationship describing $\beta$ may be shown below in Equation (7).

$$\beta = \frac{\ln\left(\frac{df_e(t)}{dD}|_\psi / \frac{df_e(t)}{dD}|_d\right)}{(D_\psi - D_d/D_d)} \quad (7)$$

In the above equation, all the parameters, except $\beta$, can be measured using suitable sensor arrangements such as a force-ultrasound system, with the help of a $f_e(t)$-$D(t)$ 210 hemodynamic loop. Thus, by optimizing the solution for Equation (7), the specific stiffness index $\beta$ of the artery wall can be calculated. Finally, by performing an additional measurement of pulse wave velocity at the diastolic blood pressure level ($C_d$), the diastolic blood pressure can be evaluated using the equation $P_d = 2 \rho C_d^2/\beta$. Finally, the continuous transmural pressure waveform $P_e(t)$ can be calculated using fundamental pressure-diameter model with the help of derived $\beta$ and $P_d$ values. The above mentioned procedure applies to each cardiac cycle, and hence the method yields beat-by-beat values of transmural blood pressure from the superficial arteries.

In yet another example implementation of the present subject matter, the elasticity of tissue surrounding the target artery along with arterial blood pressure parameters can be determined by applying a hold-down pressure ($P_N$) towards the skin at various levels. According to the present subject matter, a hold-down pressure is applied by the measurement probe on a skin of a person. The hold-down pressure is varied and the effects of the varying hold-down pressure is determined. Also, the indices indicative of the material properties of the vessel and at least one of a pressure value for a particular time instant in the pulse cycle, and a minimum pressure value, or a diastolic pressure level for each pulse cycle is determined by varying the hold-down pressure. For determining at least one of the pressure value for a particular time instant in the pulse cycle, and the minimum pressure value, and the diastolic pressure value compression-decompression pattern of the vessel at the various level of applied hold-down pressure is determined. Further, a system of models relating the applied hold-down pressure with the geometry an index of elasticity of medium between the skin or the surface and the vessel is generated. Furthermore, a system of models relating the various levels of the applied hold-down pressure with the accompanying changes in the compression-decompression pattern of the vessel, the minimum pressure value or diastolic transmural pressure level, maximum pressure value or systolic transmural pressure value, transmural pressure value at time instant, and the indices of the material properties of the vessel is also constructed. The system of models derived above are solved to determine indices of the material properties of the vessel and the minimum or the diastolic transmural pressure level. Finally, a continuous transmural pressure waveform is determined based on determined indices of the material properties of the vessel and at least one of the minimum pressure value and the diastolic transmural pressure value. An example implementation is described below.

The applied hold-down pressure can be modelled in terms of the thickness H(t) 208 and elastic contestant k of the tissue surrounding the artery as: $P_N = -k \times H(t)$. Considering an insignificant change in the material property of both the tissue and an artery within a cardiac cycles and across consecutive cycles, at the time of measurement, a non-linear model relating the applied hold-down pressure $P_N$, systolic blood pressure $P_S$ and diameter $D_S$, diastolic blood pressure $P_D$ and diameter $D_D$, and specific stiffness index $\beta$ of the artery wall is developed. In this non-linear model, all the parameters, except $\beta$, $P_s$ and $P_d$, can be directly measured using suitable sensor arrangements such as a force-ultrasound system. By applying the hold-down pressure $P_N$ at multiple levels, one can develop a family of equations relating $D_S$ and $D_D$ to $\beta$, $P_s$ and $P_d$, as given in Equation (9).

$$\begin{bmatrix} P_{N1} & e^{\beta\left(\frac{D_{s1}}{D_{d1}}-1\right)} & -1 \\ P_{N2} & e^{\beta\left(\frac{D_{s2}}{D_{d2}}-1\right)} & -1 \\ P_{N2} & e^{\beta\left(\frac{D_{s3}}{D_{d3}}-1\right)} & -1 \\ \vdots & \vdots & \vdots \\ P_{Nn} & e^{\beta\left(\frac{D_{sn}}{D_{dn}}-1\right)} & -1 \end{bmatrix} \times \begin{bmatrix} 1/P_d \\ 1 \\ P_s/P_d \end{bmatrix} = 0 \quad (9)$$

Thus, the solution of the developed model gives a true estimate of $\beta$, $P_s$ and $P_d$ over a finite number of cardiac cycles. Further, the continuous transmural pressure waveform $P_e(t)$ can be determined using the fundamental pressure-diameter model with the help of given $\beta$ and $P_d$ values. The procedure is also applicable to each cardiac cycle, and hence the method yields beat-by-beat values of blood pressure from the superficial arteries.

Figure 3:
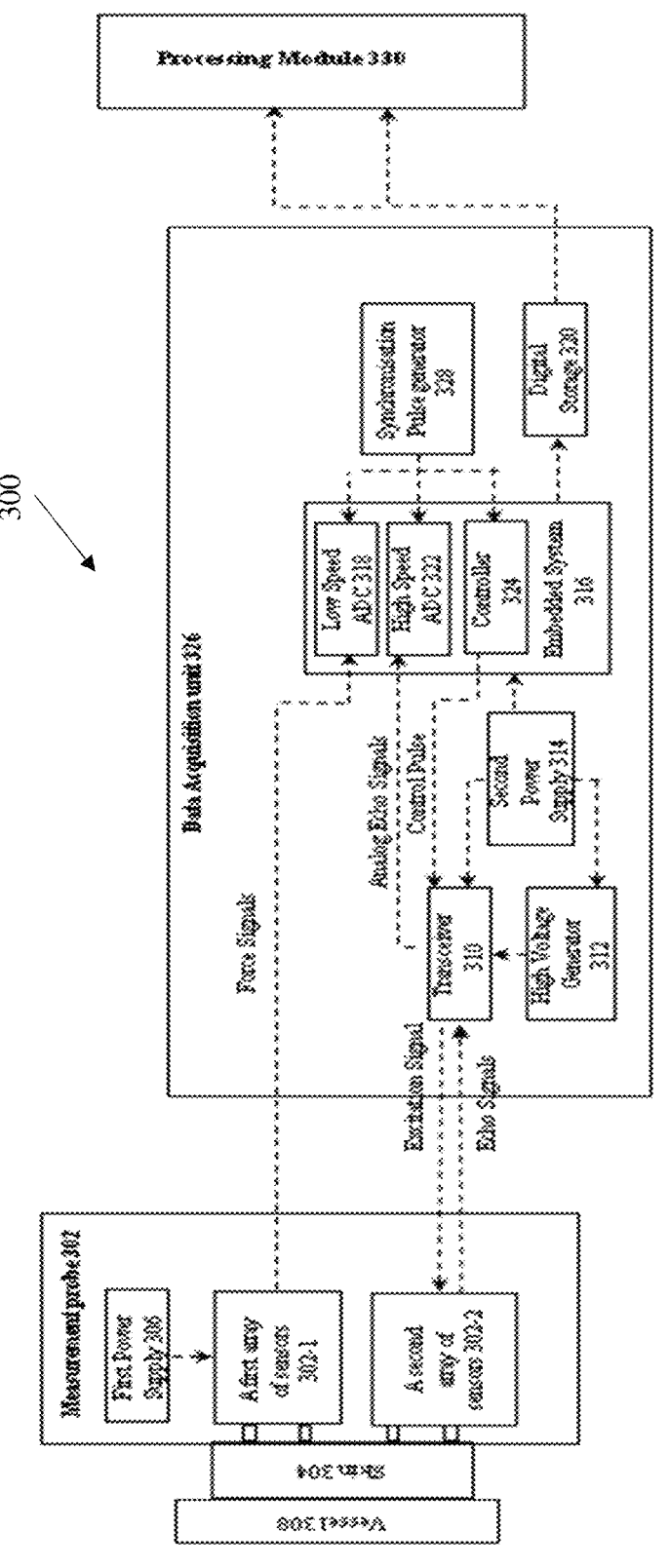
FIG. 3 shows a system 300 for measurement of blood pressure in another example implementation of the present subject matter.

FIG. 3 discloses a system 300 for determining blood pressure and continuous blood pressure waveform in an example implementation of the present subject matter. The system 300 comprises, among other things, a measurement probe 302, a data acquisition unit 326, and a processing module 330. The measurement probe 302 is similar to the measurement probe 102, the data acquisition unit 326 is similar to the data acquisition unit 104, and the processing module 330 is similar to the processing module 106. A module may include routines, programs, objects, data structures and other similar components which implements a specific task.

The measurement probe 302 comprises a first array of sensors 302-1 and a second array of sensors 302-2. The first array of sensors 302-1 and the second array of sensors 302-2 is in contact with a skin 304 of the person. The first array of sensors 302-1 and the second array of sensors 302-2 are powered by a first power supply 306 to provide operating power to the first array of sensors 302-1 and the second array of sensors 302-2. The first array of sensors determines a force exerted on the skin 304 by a vessel 308. The second array of sensors captures the dynamics of the arterial walls in the form of echo signals that are used to determine waveforms of arterial wall compression and decompression. In an example, the second array of sensors 302-2 may comprise ultrasound sensors.

To measure the arterial wall compression and decompression waveform the second array of sensors receives an excitation signal from a transceiver 310 of the data acquisition unit 326. The transceiver 310 receives the excitation signals from a high voltage generator 312. A second power supply 314 powers both the transceiver 310 and the high-voltage generator 312. The high-voltage generator 312 generates an excitation signal and provides the excitation signal to the transceiver 310 which in turn provides the excitation signal to the second array of sensors 302-2. The excitation signals cause the second array of sensors 302-2 to insonate a target region of artery through skin 304 and the echo signals reflected from the artery towards the skin 304 are detected by the second array of sensors 302-2. The reflected echo signals collected over time indicate the compression-decompression of the artery through skin 304.

Thus, the first array of sensors 302-1 detects the force signals and the second array of signals 302-2 detects the echo signals and combinedly provide the force signals and the echo signals to an embedded system 316. The force signals detected by the first array of sensors 302-1 and the echo signals detected by the second array of signals 302-2 are analog signals. A low speed analog to digital converter (ADC) 318 of the embedded system 316 converts the force signals to digital force signals and stores the digitalized force signal in a digital storage 320. Similarly, a high-speed ADC 322 of the embedded system 316 converts the echo signals into digital echo signal and store the digital echo signal in the digital storage 320. Further, the embedded system 316 also comprise a controller 324 which provide control signal to configure the transceiver 310 operation. The data acquisition unit 326 also comprises a synchronization pulse generator 328 to provide synchronization signals to the low speed ADC 318, the high-speed ADC 322, and the controller 324. This is to ensure the acquisition of signals from the first array of sensors 302-1 and the second array sensors 302-2 into digital domain are synchronized and are simultaneous without any time lags.

The digital echo signals and the digital force signals are analyzed by the processing module 330 to determine the BP. The processing module 330 extracts the digital force signals and the digital echo signals from the digital storage 320.

The processing module 330 analyzes the echo signal to determine locations of the near and far wall of the vessel 308. The processing module 330 also determines a motion waveform of the artery walls by tracking the determined locations of the walls and estimates diameter of the artery. Further, any frequency miss-matching effects between the digital force signals and the digital echo signal is corrected. The digital echo signals and the digital force signals are synchronized and any sensor offset is corrected. The digital echo signals and the digital force signals are used to generate hemodynamic curve. The hemodynamic curve provides a relationship between skin surface force (as indicated by digital force signals) to geometrical variations of the walls of the vessel 308. The geometrical variation of the vessel 308 is determined by analyzing the echo signals.

In an example, a relationship between elastic component of the blood pressure acting on arterial wall $P_e(t)$ and its skin surface force $f_e(t)$ can be represented as:

$$P_e(t) = A \times f_e(t) + B$$

wherein A and B are constants.

The sensor array 302-1 generates the skin surface force and sensor array 302-2 generates the arterial vessel wall dynamics. The hemodynamic curve is obtained from the generated force and wall dynamics signals. The processing module 330 may determine hemodynamic curves at multiple artery sites to determine the value of the constants A and B using models derived from hemodynamic curves. The hemodynamic curve captures the viscous and elastic nature of the arterial vessel wall dynamics and of interleaving tissue. The models utilize these viscous and elastic properties from hemodynamic curve to derive constants A, B, and $f_e(t)$ from of the measured surface force. When all the variables A, B, and $f_e(t)$ is known the BP component $P_e(t)$ can be calculated in a calibration-free manner. Further, the techniques described in reference to FIG. 1 may also be applied to FIG. 3 for calculating blood pressure and continuous transmural pressure waveform.

FIG. 4 illustrates a method for generating blood pressure and continuous transmural pressure waveform. It should be understood that the method steps are shown as a reference only and sequence of the method steps should not be construed as limitation. The method steps can include any additional steps in any order. Although, the method 400 may be implemented in any system, the example method 400 is provided in reference to the system 100 for ease of explanation.

At step 402, a force exerted on skin above a vessel is detected. The force is exerted by blood flowing in the vessel. At step 404, a compression-decompression waveform of the vessel below the skin is determined. To determine the compression-decompression waveform excitation signals are sent through the skin to the vessel. The echo signals reflected from the vessel is detected to determine compression-decompression of the vessel. The detected force values and compression-decompression are converted to digital values at step 406. The digital force signals and the digital compression-decompression signals are time synchronized. At step 408, indices indicative of the material properties of the vessel is determined based on non-linear relationship between the force exerted on the skin and compression-decompression pattern of the vessel below the skin. To determine the indices of the material properties of the vessel non-linear changes in the force detected on the skin and the compression-decompression pattern of the vessel below the skin is captured. At step 410, blood pressure and continuous transmural pressure waveform is generated based on the indices of the material properties of the vessel. To determine the blood pressure and continuous transmural pressure waveform based on the indices of the material properties of the vessel, the instantaneous transit time and a pulse wave velocity of blood pulse wave within the vessel are estimated. Based on the estimation at least one of the pressure value for a particular time instant in the pulse cycle, and the minimum pressure value, and the diastolic pressure value for a pulse cycle is determined. Based on at least one of the pressure value for a particular time instant in the pulse cycle, and the minimum pressure value, and the diastolic pressure value and the indices of the material properties of the vessel, blood pressure and continuous transmural pressure waveform is generated.

Thus, the present invention provides a convenient, unobtrusive, and low-cost device for non-invasive measurement of BP parameters (specifically, the central BP parameter), arterial pressure waveforms, and other vascular health markers without requiring any subject- or population-specific initial calibration or frequent re-calibration procedures. The system works for any demographic population, without the need for further empirical or analytical models pertaining to the specific population. The system enables real-time measurement from the superficial arteries and helps in continuous monitoring of BP parameters. The system simultaneously measures percutaneously transferred arterial pressure (using force signals) from the skin surface, and enables continuous capturing of high-fidelity waveforms of dynamic vascular geometry using the echo signals.

In an example, any superficial and large arteries, such as common carotid arteries, femoral arteries, brachial arteries, aorta can be used for measuring the BP.

With help of echo signals, lumen diameter, instantaneous distension and diameter waveforms, intima-media thickness (wall thickness), instantaneous wall thickness waveform, and displacement, velocity, and acceleration of arterial walls can be measured.

The system of the present subject matter enables the central BP parameters to be directly measured using hemodynamic curves without any calibration procedure and without relying on any subject- or population-specific mathematical transfer functions.

The BP and arterial geometry measured using the device further enables the estimation of vascular health markers and stiffness parameters. For example, a local stiffness of any superficial and large arteries, such as common carotid arteries, femoral arteries, brachial arteries, aorta, etc. may be using the hemodynamic curves. Local stiffness indices, such as arterial compliance, Young's modulus of elasticity, pressure-strain elastic modulus, arterial distensibility, stiffness index β, vessel wall rigidity coefficient, local pulse wave velocity (PWV), systolic and diastolic PWV, change in PWV within a cardiac cycle, incremental PWV, local pulse transit time, wave reflection time, characteristic impedance, augmentation index, etc., can also be measured. Further, viscous properties, such as arterial wall viscosity index, wall buffering function, etc. can also be measured by the system of the present subject matter.

In the specification, there has been disclosed exemplary embodiments of the invention. Although specific terms are employed, they are used in a generic and descriptive sense only and not for purposes of limitation of the scope of the invention.

We claim:

1. A system for generating blood pressure and continuous transmural pressure waveform in real-time, the system comprising:

a measurement probe (302) positioned in contact with skin, the measurement probe (302) comprises:

a first array of sensors comprising at least one sensor to detect a force exerted by a vessel on the skin in real-time;

a second array of sensors comprising at least one sensor to determine a compression-decompression pattern of a vessel cross-section below the skin in real-time;

a data acquisition unit (326), coupled to the measurement probe (302), to:

receive the force detected by the first array of sensors in real-time, and receive the compression-decompression pattern determined by the second array of sensors in real-time;

a processing module (330), coupled to the data acquisition unit (326), to:

determine indices indicative of material properties including specific stiffness index (β), elastic modulus, viscoelasticity, arterial compliance, and pulse wave velocity, of the vessel based on a relationship between the force exerted on the skin and the compression-decompression pattern of the vessel below the skin in real-time; and generate the blood pressure and the continuous transmural pressure waveform based on the determined indices of the material properties of the vessel in real-time, wherein the force exerted on the skin=

$$E_s\, x_{-}\frac{1}{H(t)} + \eta_s \frac{d}{dt}\left(\frac{1}{H(t)}\right),$$

wherein the compression-decompression pattern of the vessel below the skin=$\propto(1/D(t)) \propto 1/(P(t))$, and where $E_s$ is the elastic modulus, $H(t)$ is the compression decompression pattern, $D(t)$ is a quasiperiodic expansion/contraction of a luminal diameter of the vessel, $P(t)$ is a pulsative transmural pressure of the vessel acting towards a radial direction of the vessel, and $\eta_s$ is a viscoelastic coefficient for vessel layers between a proximal wall of the vessel and the skin.

2. The system as claimed in claim 1, wherein generating the blood pressure and the continuous transmural pressure waveform based on the indices of the material properties comprises determining, by the processing module (330), at least one of a pressure value for a particular time instant in the pulse cycle, a minimum pressure value, and a diastolic pressure value for each pulse cycle.

3. The system as claimed in claim 2, wherein determining at least one of the pressure value for a particular time instant in the pulse cycle, the minimum pressure value, and the diastolic pressure value by the processing module (330) comprises:

estimating instantaneous transit time and pulse wave velocity of a blood pulse wave within the vessel corresponding to the at least one of the pressure value for a particular time instant in the pulse cycle, the minimum pressure value, and the diastolic pressure value; and determining the indices of the material properties of the vessel.

4. The system as claimed in claim 3, wherein determining the indices of the material properties of the vessel comprises capturing non-linear changes in the force detected on the skin and the compression-decompression pattern of the vessel below the skin using at least one of the following nonlinear relationships:

relating the indices of the material properties of the vessel to an elastic component of instantaneous force detected on the skin, the peak change in the elastic component of the instantaneous force and vessel diameter waveform, and extrema of the vessel diameter waveform;

relating the indices of the material properties of the vessel to blood pulse wave velocity, vessel diameter, and relative change of force detected on the skin to diameter, respectively, at multiple time instants and the peak gradient of vessel diameter; and relating the indices of the material properties of the vessel to a relative change in the force detected on the skin to the vessel diameter and the vessel diameter gradient at multiple time instants.

5. The system as claimed in claim 1, wherein the data acquisition unit (326) comprises:

a transceiver (310) to:
    send excitation signals through the skin to the vessel; and
    detect echo signals reflected by the vessel wherein the echo signals are used to determine the compression-decompression pattern of the vessel; and
  an embedded system (316) to:
    receive a value of the force detected by the first array of sensors, wherein the value of force detected is an analog value;
    receive the echo signals from the transceiver (310), wherein the echo signals are in analog form; and
    convert the analog value of the force and the analog value of the echo signals to digital values.

6. A method for generating blood pressure and continuous transmural pressure waveform in real-time, the method comprising:

detecting a force value exerted on skin above a vessel in real-time;
  determining compression-decompression waveform of the vessel below the skin in real-time;
  converting the detected force and the determined compression-decompression waveform to digital signals in real-time;
  determining indices indicative of the material properties including specific stiffness index (β), elastic modulus, viscoelasticity, arterial compliance, and pulse wave velocity of the vessel based on a non-linear relationship between the force exerted on the skin and the compression-decompression pattern of the vessel below the skin based on the digital signal in real-time; and
  generating the blood pressure and the continuous transmural pressure waveform based on the indices of the material properties of the vessel in real-time,
    wherein the force exerted on the skin=

$$E_s \; x_{-\frac{1}{H(t)}} + \eta_s \frac{d}{dt}\left(\frac{1}{H(t)}\right),$$

wherein the compression-decompression pattern of the vessel below the skin=∝(1/D(t)) ∝1/(P(t)), and
    where $E_s$ is the elastic modulus, H(t) is the compression decompression pattern, D(t) is a quasiperiodic expansion/contraction of a luminal diameter of the vessel, P(t) is a pulsative transmural pressure of the vessel acting towards a radial direction of the vessel, and $\eta_s$ is a viscoelastic coefficient for vessel layers between a proximal wall of the vessel and the skin.

7. A method as claimed in claim 6, the method further comprises:

sending excitation signals through the skin to the vessel; and
  detecting echo signals reflected by the vessel wherein the echo signals indicate the compression-decompression pattern of the vessel.

8. The method as claimed in claim 6, further comprises synchronizing the digital force signals and the digital compression-decompression signals.

9. The method as claimed in claim 6, wherein the generating the blood pressure and continuous transmural pressure waveform based on the indices of the material properties comprises of determining at least one of a pressure value for a particular time instant in the pulse cycle, a minimum pressure value, and a diastolic pressure value for each pulse cycle.

10. The method as claimed in claim 9, wherein determining at least one of the pressure value for a particular time instant in the pulse cycle, and the minimum pressure value, and the diastolic pressure value by a processing module (330) comprises of estimating the transit features and wave velocity of blood pulse wave within the vessel corresponding to the at least one of the pressure value for a particular time instant in the pulse cycle, the minimum pressure value, and the diastolic pressure level for each pulse cycle and determining the indices of the material properties of the vessel.

11. The method as claimed in claim 10, wherein determining the indices of the material properties of the vessel comprises of capturing non-linear changes in the force detected on the skin and the compression-decompression pattern of the vessel below the skin or surface.

12. A method for generating blood pressure and continuous transmural pressure waveform in real-time, the method comprising:

applying hold-down pressure by a measurement probe (302) on a skin above a vessel in real-time;
  varying the hold-down pressure to multiple levels in a controlled manner in real-time;
  capturing the results of the varying hold-down pressure on a geometry of the vessel and a medium surrounding the vessel in real-time;
  determining indices indicative of material properties including specific stiffness index (β), elastic modulus, viscoelasticity, arterial compliance, and pulse wave velocity of the vessel based on a relationship between a force exerted on the skin and a compression-decompression pattern of the vessel below the skin in real-time; and
  generating a blood pressure and a continuous transmural pressure based on captured results in real-time,
    wherein the force exerted on the skin=

$$E_s \; x_{-\frac{1}{H(t)}} + \eta_s \frac{d}{dt}\left(\frac{1}{H(t)}\right),$$

wherein the compression-decompression pattern of the vessel below the skin=∝(1/D(t)) ∝1/(P(t)), and
    where $E_s$ is the elastic modulus, H(t) is the compression decompression pattern, D(t) is a quasiperiodic expansion/contraction of a luminal diameter of the vessel, P(t) is a pulsative transmural pressure of the vessel acting towards a radial direction of the vessel, and $\eta_s$ is a viscoelastic coefficient for vessel layers between a proximal wall of the vessel and the skin.

13. The method as claimed in claim 12, wherein generating the blood pressure and the continuous transmural pressure based on capturing the results of the varying hold-down pressure level comprises determining indices indicative of the material properties of the vessel and at least one of a pressure value for a particular time instant in the pulse cycle, a minimum pressure value, and diastolic pressure value for each pulse cycle.

14. The method as claimed in claim 13, wherein determining the indices of the material properties of the vessel and at least one of the pressure value for a particular time instant in the pulse cycle, and the minimum pressure value, and the diastolic pressure value for each pulse cycle comprises:

determining the compression-decompression pattern of the vessel at the various level of applied hold-down pressure;

constructing of a system of models relating the applied hold-down pressure with the geometry and an index of elasticity of medium between the skin or the surface and the vessel;

constructing of a system of models relating the various levels of the applied hold-down pressure with the determined changes in the compression-decompression pattern of the vessel, the minimum pressure value or a diastolic transmural pressure level, a maximum pressure value or a systolic transmural pressure value, a transmural pressure value at time instant, and the indices of the material properties of the vessel;

solving the system of models to determine the indices of the material properties of the vessel and at least one of the minimum pressure value and the diastolic transmural pressure value; and determining a continuous transmural pressure waveform based on determined indices of the material properties of the vessel and at least one of the minimum pressure value and the diastolic transmural pressure value.

* * * * *